(12) United States Patent
Gallagher et al.

(10) Patent No.: US 6,528,512 B1
(45) Date of Patent: Mar. 4, 2003

(54) PYRIMIDINE COMPOUNDS USEFUL IN TREATING CYTOKINE MEDIATED DISEASES

(75) Inventors: Timothy F. Gallagher, Harleysville, PA (US); Susan M. Thompson, Phoenixville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/602,722

(22) Filed: Jun. 26, 2000

Related U.S. Application Data

(62) Division of application No. 09/142,719, filed as application No. PCT/US97/04121 on Mar. 13, 1997, now Pat. No. 6,096,748.
(60) Provisional application No. 60/013,357, filed on Mar. 13, 1996, provisional application No. 60/013,358, filed on Mar. 13, 1996, and provisional application No. 60/013,359, filed on Mar. 13, 1996.

(51) Int. Cl.$^7$ ................... A61K 31/444; A61K 31/506; C07D 401/04
(52) U.S. Cl. ................... 514/256; 514/266.21; 544/284; 544/328
(58) Field of Search ................... 544/328, 284; 514/256, 266.21

(56) References Cited

U.S. PATENT DOCUMENTS

| | | | |
|---|---|---|---|
| 4,438,117 A | 3/1984 | Cherkofsky et al. | 424/251 |
| 4,500,533 A | 2/1985 | Matsumoto | 514/256 |
| 4,504,482 A | 3/1985 | Lesher et al. | 514/275 |
| 5,507,974 A | 4/1996 | Gompper et al. | 252/299.01 |
| 6,096,748 A | * 8/2000 | Gallagher et al. | 514/256 |

FOREIGN PATENT DOCUMENTS

| | | |
|---|---|---|
| EP | 0 164 204 | 12/1985 |
| EP | 0 233 461 | 8/1987 |
| WO | WO 95/15758 | 6/1995 |
| WO | WO 96/21654 | 7/1996 |

OTHER PUBLICATIONS

Borovik et al., Chem. Abstracts No. 115:183224, Oct. 1991.*
Kabbe, Heterocycles from carboxylic acid derivatives., Ann. Chem., Justus Liebigs, vol. 704, pp. 144–49, 1967.*
Paul, R. et al., "Preparation of substituted N–phenyl–4–aryl–2–pyrimidinamines as mediator release inhibitors", *Journal of Medical Chemistry*, American Chemical Society, Washington, US, vol. 36, No. 19, 1993, pp. 2716–2725.
Moehrle, et al., Chem., abstr., vol. 121, No. 15, p. 1076, col. 1, Oct. 10, 1994.
Hung, et al. Chem. abstr., vol.101, No.25, p. 765, col. 1–col. 2, Dec. 17, 1984.
Bennett e al., J. Med. Chem., vol. 21, No. 7, pp. 623–628, 1978.

* cited by examiner

*Primary Examiner*—Deepak Rao
(74) *Attorney, Agent, or Firm*—Dara L. Dinner; Stephen Venetianer; Charles M. Kinzig

(57) ABSTRACT

This invention relates to the novel amino substituted pyrimidine compounds of Formulas (I), (II) and (III), and pharmaceutical compositions comprising a compound of these Formulas and a pharmaceutically acceptable diluent or carrier.

This invention also relates to a method of inhibiting CSBP kinase and cytokines mediated by this kinase, for the treatment of cytokine mediated diseases, in mammals, by administration of a compound of Formula (I), (II) or (III).

16 Claims, No Drawings

PYRIMIDINE COMPOUNDS USEFUL IN TREATING CYTOKINE MEDIATED DISEASES

This application is a divisional of Ser. No. 09/142,719 filed Sep. 14, 1998 now U.S. Pat. No. 6,096,748 which is a 371 of PCT/US97/04121 filed Mar. 13, 1997 which claims benefit of U.S. Provisional Application No. 60/013,357 filed Mar. 13, 1996; 60/013,358 filed Mar. 13, 1996 and 60/013,359 filed Mar. 13, 1996.

FIELD OF THE INVENTION

This invention relates to a novel group of pyximidine compounds, processes for the preparation thereof, the use thereof in treating cytokine mediated diseases and pharmaceutical compositions for use in such therapy.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoartritis, endotoxemia and/or toxic shock syndrome, other acute or chronic inflammatory disease states such as the inflammatory reaction induced by endotoxin or inflammatory bowel disease: tuberculosis, atherosclerosis, muscle degeneration, cachexia, psoriatic arthritis, Reitefs syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T Cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Monokines, specifically TNF, are implicated in activated T-cell mediated HIV protein expression and/or virus replication by playing a role in maintaining T lymphocyte activation. Therefore, interference with monokine activity such as by inhibition of monokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T-cells, are targets for viral replication and the level of viral replication is dependent upon the activation state of the cells. [See Rosenberg et al., The Immunopathogenesis of HIV Infection, Advances in Immunology, Vol. 57, (1989)]. Monokines, such as TNF, have been shown to activate HIV replication in monocytes and/or macrophages [See Poli, et. al., Proc. Natl. Acad. Sci., 87:782–784 (1990)], therefore, inhibition of monokine production or activity aids in limiting HIV progression as stated above for T-cells.

TNF has also been implicated in various roles with other viral infections, such as the cytomegalia virus (CMV), influenza virus, and the herpes virus for similar reasons as those noted.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractantlactivation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neuerophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for treatment, in this field, for compounds which are cytokine suppressive anti-inflaimnatory drugs, i.e. compounds which are capable of inhibiting cytokines, such as IL-1, IL-6, IL-8 and TNF.

SUMMARY OF THE INVENTION

This invention relates to the novel compounds of Formulas (I), (II), and (III) and pharmaceutical compositions comprising a compound of Formula (I), (II), or (III), respectively, and a pharmaceutically acceptable diluent or carrier.

This invention also relates to a method of inhibiting cytokines and the treaunent of a cytokine mediated disease, in a mammal in need thereof, which comprises administering to said mammal an effective amount of a compound of Formula (I), (II), or (III).

This invention more specifically relates to a method of inhibiting the production of IL-1 in a mammal in need thereof which comprises administering to said mammal an effective amount of a compound of Formula (I), (II), or (III).

This invention more specifically relates to a method of inhibiting the production of IL-8 in a mammal in need thereof which comprises administering to said mamrnal an effective amount of a compound of Formula (I), (II), or (III).

This invention more specifically relates to a method of inhibiting the production of TNF in a mammal in need thereof which comprises administering to said mammal an effective amount of a compound of Formula (I), (II), or (III).

DETAILED DESCRIMION OF THE INVENTION

The novel compounds of this invention are represented by the structure having the formula:

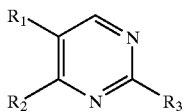

(I)

wherein:

$R_1$ is 4pyridyl, 4pyrimidinyl, 4-quinazolinyl, 4-quinolyl, or 6-isoquinolinyl, which rings are optionally substituted with one or two substituents, each of which is independently selected from Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, anino, mono and di- $C_{1-6}$ allyl substituted amino, or $N(R_{10})C(O)R_b$;

Y is $X_1$—$R_a$;

$X_1$ is oxygen or sulfur;

$R_a$ is $C_{1-6}$alkyl, aryl, aryl$C_{1-6}$alkyl, heterocyclic, heterocyclyl$C_{1-6}$ alkyl, heteroaryl, hetrroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl, wherein each of these moieties may be optionally substituted;

$R_2$ is an optionally substituted auyl or optionally substituted heteroaryl group, provided that both $R_1$ and $R_2$ are not the same heteroaryl group;

and when $R_2$ is an optionally substituted aryl ring, the ring is substituted by one or two substituents, each of which is independently selected, and, which, for a 4-phenyl, 4-naphth-1-yl or 5-naphth-2-yl substituent, is halo, cyano, —C(Z)NR$_{13}$R$_{14}$, —C(Z)OR$_{23}$, —(CR$_{10}$R$_{20}$)$_n$ COR$_{36}$, —SR$_{15}$, —SOR$_{15}$, —OR$_{36}$, halo-substituted-C$_{1-4}$ alkyl, C$_{1-4}$ alkyl, —ZC(Z)R$_{36}$, —NR$_{10}$C(Z)R$_{23}$, or —(CR$_{10}$R$_{20}$)$_n$ NR$_{10}$R$_{20}$ and which, for other positions of substitution, is halo, cyano, —C(Z)NR$_{16}$R$_{26}$, —C(Z)OR$_8$, —(CR$_{10}$R$_{20}$)$_n$ COR$_8$, —S(O)$_m$R$_8$, —OR$_8$, halo-substituted-C$_{1-4}$ alkyl, —C$_{1-4}$ alkyl, —(CR$_{10}$R$_{20}$)$_n$NR$_{10}$C(Z)R$_8$, —NHS(O)$_m$R$_7$, —NHS(O)$_m$NR$_{13}$R$_{14}$, —NR$_7$S(O)$_m$R$_7$, —NR$_7$S(O)$_{m'}$NR$_{13}$R$_{14}$ wherein m' is 1 or 2, —ZC(Z)R$_8$ or —(CR$_{10}$R$_{20}$)$_n$ NR$_{16}$R$_{26}$;

and when $R_2$ is an optionally substituted heteroaryl group, the substituent groups include one or two substituents each of which is independently selected from $C_{1-4}$ alkyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatom selected from oxygen, sulfur or $NR_{12}$;

m is 0 or an integer of 1 or 2;

n is 0 or an integer of 1 or 2;

$R_3$ is hydrogen, $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the alkyl, aryl, arylalkyl, heteroaryl, heteroaryl alkyl, heterocyclic and heterocyclic alkyl moieties of $R_7$, and $R_8$ may be optionally substituted;

$R_5$ and $R_6$ are each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

Z is oxygen or sulfur;

$R_7$ is $C_{1-10}$ alkyl, $C_{3-7}$ cycloalkyl, aryl, arylalkyl, heterocyclyl, heterocyclyl-$C_{1-10}$alkyl, heteroaryl or heteroarylalkyl;

$R_8$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_9$ is hydrogen, —C(Z)R$_8$ or optionally substituted $C_{1-10}$ alkyl, $S(O)_2R_7$, optionally substituted aryl or optionally substituted aryl-$C_{1-4}$ alkyl;

$R_{10}$ and $R_{20}$ is each independenty selected from hydrogen or $C_{1-6}$ alkyl;

$R_{11}$ is hydrogen, cyano, $C_{1-4}$ alkyl, $C_{3-7}$ cycloalkyl or aryl;

$R_{12}$ is $R_{10}$ or C(Z)—$C_{1-4}$ alkyl, optionally substituted aryl, optionally substituted aryl$C_{1-4}$ alkyl, or $S(O)_2R_7$;

$R_{13}$ and $R_{14}$ is each independently selected from hydrogen or $C_{1-4}$ alkyl or $R_{13}$ and $R_{14}$ together with the nitrogen to which they are attached form a heterocyclic ring of 5 to 7 members which ring optionally contains an additional heteroatom selected from oxygen, sulfur or $NR_{22}$;

$R_{15}$ is hydrogen, $C_{1-4}$ alkyl $C_{2-4}$ alkenyl, $C_{2-4}$ alkynyl or $NR_{13}R_{14}$, provided that the moiety —SR$_{15}$ is not —SNR$_{13}$R$_{14}$ and the moiety —S(O)R$_{15}$ is not —SOH;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{12}$;

$R_{22}$ is $R_{10}$ or C(Z)—$C_{1-4}$ alkyl;

$R_{23}$ is $C_{1-4}$ alkyl halo-substituted-$C_{1-4}$ alkyl, or $C_{3-5}$ cycloalkyl;

$R_{36}$ is hydrogen or $R_{23}$;

or a pharmaceutically acceptable salt thereof.

Suitable heteroaryl moieties for $R_1$ and $R_2$ are 4-pyridyl, 4-pyrimidinyl, 4-quinazolinyl, 4-quinolyl, or 6-isoquinolinyl, 1-irnidazolyl, 1-benzimidazolyl and thiophene. Preferably the heteroaryl ring is a 4-pyridyl, 4-pyrimidinyl, 4-quinazolinyl, 4-quinolyl, or 6-isoquinolinyl ring. More preferably the heteroaryl group is a 4-pyridyl, or 4-pyrimidinyl ring. Preferably, the 4-pyridyl group is substituted in the 2-position and the 4-pyrimidinyl group is substituted at the 2- or 4-position.

Each of these heteroaryl rings may be optionally substituted with one or two substituents, each of which is independently selected from Y, $NHR_a$, optionally substituted $C_{1-4}$alkyl, halogen, hydroxyl, optionally substituted $C_{1-4}$ alkoxy, optionally substituted $C_{1-4}$ alkylthio, $C_{1-4}$ alkylsulfmyl, $CH_2OR_{12}$, amino, mono and di-$C_{1-6}$ alkyl substituted amino, or $N(R_{10})C(O)R_b$.

Y is suitably Y is $X_1$—$R_a$; and $X_1$ is oxygen or sulfur, preferably oxgyen. $R_a$ is suitably a $C_{1-6}$ alkyl, aryl, aryl$C_{1-6}$alkyl, heterocyclic, heterocyclyl$C_{1-6}$ alkyl, heteroaryl, heteroaryl$C_{1-6}$alkyl group, wherein each of these moieties may be optionally substituted.

$R_b$ is suitably hydrogen, $C_{1-6}$ alkyl, $C_{3-7}$ cycloalkyl, aryl, aryl$C_{1-4}$ alyl, heteroaryl, heteroaryl$C_{1-4}$ alkyl, heterocyclyl, or heterocyclyl$C_{1-4}$ alky, wherein each of these moieties may be optionally substituted as defined herein.

When the $R_1$ substituent is Y, and $R_a$ is aryl, it is preferably phenyl or naphthyl. When $R_a$ is aryl alkyl, it is preferably benzyl or napthylmethyl. When $R_a$ is herterocyclic or heterocyclic alkyl moiety, the heterocyclic portion is preferably pyrrolindinyl, piperidine, morpholino, tetrahydropyran, tetrahydrothiopyranyl, tetrahydrothipyransulfinyl, tetrahydrothio-pyransulfonyl, pyrrolindinyl, indole, or piperonyl. It is noted that the heterocyclic rings herein may contain unsaturation, such as in a tryptamine ring.

The $R_a$ aryl, heterocyclic and heteroaryl rings may be optionally substituted one or more times independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy: $S(O)_m$alkyl and $S(O)_m$aryl (wherein m is 0, 1, or 2); $C(O)OR_{11}$, such as $C(O)C_{1-4}$ alkyl or C(O)OH moieties; $C(O)R_{11}$; —$OC(O)R_c$; O—$(CH_2)$s-O—, such as in a ketal or dioxyalkylene bridge; amino; mono- and di-$C_{1-6}$ alkylsubstituted amino; —$N(R_{10})C(O)R_b$; —$C(O)NR_{10}R_{20}$; cyano, nitro, or an N-heterocyclyl ring which ring has from 5 to 7 mnembers and optionally contains an additional heteroatomn selected from oxygen, sulfur or $NR_{15}$; aryl, such as phenyl; an optionally substituted arylalkyl, such as benzyl or phenethyl; aryloxy, such as phenoxy; or arylalkyloxy such as benzyloxy. Wherein $R_c$ is optionally substituted $C_{1-6}$ aklyl, $C_{3-7}$ cycloalkyl, aryl, aryl$C_{1-4}$ alkyl, heteroaryl, heteroaryl$C_{1-4}$allcyl, heterocyclyl, or heterocyclyl$C_{1-4}$ alkyl moieties.

Preferably, the $R_a$ groups include benzyl, halosubstituted benzyl, napthylmethyl, phenyl, halosubstituted phenyl, aminocarbonylphenyl, alkylphenyl, cyanophenyl, alkylthiophenyl, hydroxyphenyl, alkoxyphenyl, morpholinopropyl, piperonyl, piperidin-4-yl, alkyl substituted piperidine, such as 1-methyl piperidine, or 2,2,6,6-tetramethylpiperidin-4-yl.

Preferably, when the substituent is $NHR_a$ then $R_a$ is aryl, such as phenyl or napthyl; arylalkyl such as benzyl or naphtylmethyl; halosubstituted arylalkyl, halosubstituted aryl; heterocyclic alkyl, such as morpholinopropyl; hydroxy alkyl; alkyl-1-piperidinearboxylate: heterocyclic, such as piperonyl, or piperidinyl; alkyl substituted heterocyclic, such as alkyl substituted piperidine; halosubstituted heterocyclic; or aryl substituted heterocyclic.

Preferably, when the $R_1$ substituent is an optionally substituted $C_{1-4}$ alkoxy or $C_{1-4}$ alkylthio, the alkyl chain may be substituted by halogen, such as fluorine, chlorine, bromine or iodine; hydroxy, such as hydroxyethoxy; $C_{1-10}$ alkoxy, such as a methoxymethoxy, $S(O)_m$ alkyl, wherein m is 0, 1 or 2: amino, mono & di-substituted amino, such as in the $NR_7R_{17}$ group, i.e. tert-butylaminoethoxy; or where the $R_7R_{17}$ may together with the nitrogen to which they are attached cyclize to form a 5 to 7 membered ring which optionally includes an additional heteroatom selected from O/N/S, $C_{1-10}$ alkyl, cycloalkyl, or cycloalkyl alkyl group, such as methyl, ethyl, propyl, isopropyl, t-butyl, etc. or cyclopropyl methyl; or halosubstituted $C_{1-10}$ alkyl, such as $CF_3$.

Preferred substituents for the heteroaryl ring $R_1$ is $C_{1-4}$ alkyl, $NH_2$ or monosubstituted $C_{1-4}$alkyl amino, i.e. wherein both $R_{10}$ and $R_{20}$ are preferably hydrogen or one of $R_{10}$ and $R_{20}$ is hydrogen and the other is a $C_{1-4}$ alkyl. Preferably, when the substituent is a $C_{1-4}$ alkyl group it is methyl, and when the substitutent is the mono-substiuted amino, it is preferably —$NH(CH_3)$.

For the purposes herein when the RI is a 4-pyriinidinyl moiety the "core" pyrimidinyl is referred to as having the formula:

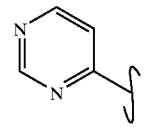

When the $R_1$ (or $R_2$) 4-pyrimidinyl moiety is substituted it is preferably substituted in at least one of the following position by the moiety $Y_3$ and $Y_4$ which are referred to herein in greater detail as optional substituents on the heteroaryl rings $R_1$ and $R_2$.

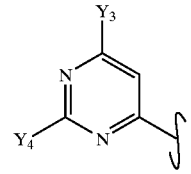

As the nomenclature will change when either $Y_3$ or $Y_4$ is substituted, for the purposes herein when $Y_4$ but not $Y_3$ is the substituted position it is referred to as the 2- position. When $Y_3$ but not $Y_4$ is the substituted position it is referred to as the 4-position and the point of attachment of the pyrimidinyl ring is not the 6-position.

Suitable aryl groups for $R_2$ include optionally substituted phenyl, naphth-1-yl or naphth-2-yl. Preferably $R_2$ is an optionally substituted phenyl. These aryl rings may be optionally substituted by one or two substituents, each of which is independently selected, and which, for a 4-phenyl, -naphth-1-yl or 5-naphth-2-yl substituent, is halo, cyano, —$C(Z)NR_{13}R_{14}$, —$C(Z)OR_{23}$, —$(CR_1OR_2O)_n$ $COR_{36}$, —$SR_{15}$, —$SOR_{15}$, —$OR_{36}$, halo-substituted-$C_{1-4}$ alkyl, $C_{1-4}$ alkyl, —$ZC(Z)R_{36}$, —$NR_{10}C(Z)R_{23}$, or —$(CR_{10}R_{20})_n NR_{10}R_{20}$ and which, for other positions of substitution, is halo, cyano, —$C(Z)NR_{16}R_{26}$, —$C(Z)OR_8$, —$(CR_{10}R_{20})_n COR_8$, —$S(O)_m R_8$, —$OR_8$, halo-substituted-$C_{1-4}$ alkyl, —$C_{1-4}$ alkyl, —$(CR_{10}R_{20})_n NR_{10}C(Z)R_8$, —$NHS(O)_m R_7$, —$NHS(O)_m NR_{13}R_{14}$, —$NR_7 S(O)_m R_7$, —$NR_7 S(O)_{m'} NR_{13}R_{14}$ wherein m' is 1 or 2, —$ZC(Z)R_8$ or —$(CR_{10}R_2O)_n NR_{16}R_{26}$.

Preferred substitutions for $R_2$ when it is a 4-phenyl, 4naphth-1-yl or 5-naphth-2-yl moiety are one or two substituents each independently selected from halogen, —$SR_{15}$, —$SOR_{15}$, —$OR_{36}$, or —$(CR_{10}R_{20})_n NR_{10}R_{20}$, and for other positions of substitution on these rings preferred substitution is halogen, —$S(O)_m R_8$, —$OR_8$, $(CR_1 OR_{20})_n NR_{16}R_{26}$, —$(CR_{10}R_{20})_n NR_{10}C(Z)R_8$ and —$NR_7 S(O)_m R_7$. More preferred substituents for the 4-position in phenyl and naphth-1-yl and on the 5-position in naphth-2-yl include halogen, especially fluoro and chloro, and —$SR_{15}$ and $S(O)R_{15}$ wherein $R_{15}$ is preferably a $C_{1-4}$ alkyl, more preferably methyl; of which fluoro is especially preferred. Preferred substituents for the 3-position in phenyl and naphth-1-yl include: halogen, especially chloro; —$OR_8$, especially $C_{1-4}$ alkoxy; amino; —$NR_{10}C(Z)R_8$, especially —$NHCO(C_{1-10}alkyl)$; and —$NR_{10}S(O)_m R_{11}$, especially $NHSO_2(C_{1-10}$ alkyl). Preferably, the aryl group is an unsubstituted or substituted phenyl moiety. More preferably, it is phenyl or phenyl substituted at the 4-position with fluoro and/or substituted at the 3-position with fluoro, chloro, $C_{1-4}$ alkoxy, methanesulfonamido or acetamido.

Suitably, $R_3$ is -hydrogen, $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the aryl, arylalkyl, heteroaryl, heteroaryl alkyl, heterocyclic and heterocyclic alkyl moieties of $R_5$, $R_6$, $R_7$, $R_8$, $R_{10}$, and $R_{11}$ may be optionally substituted as herein defined.

In a preferred subgenus of compounds of formula (I), $R_1$ is 4-pyidyl, 2-alkyl-4-pyridyl, 2-$NR_{10}R_{20}$opyridyl, 4pyrirridinyl, 2-alkylfpyrimidinyl, 2—$NR_{10}R_{20}$-4pyrimidinyl, or 4quinolyl; $R_2$ is an optionally substituted phenyl group. More preferably $R_2$ is phenyl or phenyl substituted by fluoro, chloro, $C_{1-4}$ alkoxy, $S(O)_m C_{1-4}$ alkyl, methanesulfonamido or acetamido.

Another aspect of the present invention are the novel compounds of Formula (II):

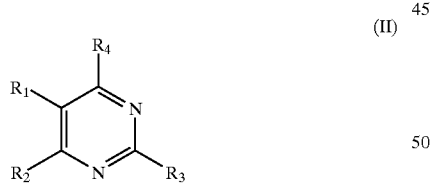

(II)

wherein:
$R_1$ is 4-pyridyl, 4-pyrimidinyl, 4-quinazolinyl, 4-quinolyl, or 6-isoquinolinyl, which rings are optionally substituted with one or two substituents, each of which is independently selected from Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2 OR_{12}$, amino, mono and di-$C_{1-6}$ alkyl substituted amino, or $N(R_{10})C(O)R_b$;
Y is $X_1$—$R_a$;
$X_1$ is oxygen or sulfur; p1 $R_a$ is $C_{1-6}$alkyl, aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$alkyl, wherein each of these moieties may be optionally substituted;

$R_2$ is an optionally substituted aryl or optionally substituted heteroaryl group, provided that both $R_1$ and $R_2$ are not the same heteroaryl group; wherein when one $R_2$ is an optionally substituted aryl ring, the ring is substituted by one or two substituents, each of which is independently selected, and which, for a 4-phenyl, 4-naphth-1-yl or 5-naphth-2-yl substituent, is halo, cyano, —$C(Z)NR_{13}R_{14}$, —$C(Z)OR_{23}$, $CR_{10}R_{20})_n COR_{36}$, —$SR_{15}$, —$S(O)R_{15}$, —$OR_{36}$, halo-substituted-$C_{1-4}$ alkyl, $C_{1-4}$ alkyl, —$ZC(Z)R_{36}$, —$NR_{10}C(Z)R_{23}$, or —$(CR_{10}R_{20})_n NR_{10}R_{20}$ and which, for other positions of substitution, is halo, cyano, —$C(Z)NR_{16}R_{26}$, —$C(Z)OR_8$, —$(CR_{10}R_{20})_n COR_8$, —$S(O)_m R_8$, —$OR_8$, halo-substituted-$C_{1-4}$ alkyl, —$C_{1-4}$ alkyl, —$(CR_{10}R_{20})_n NR_{10}C(Z)R_8$, —$NHS(O)_m R_7$, —$NHS(O)_m NR_{13}R_{14}$, —$NR_7 S(O)_m R_7$, —$NR_7 S(O)_{m'} NR_{13}R_{14}$ wherein m' is 1 or 2, —$ZC(Z)R_8$ or —$(CR_{10}R_{20})_n NR_{16}R_{26}$; and when $R_2$ is an optionally substituted heteroaryl group, the substituent groups include one or two substituents each of which is independently selected from $C_{1-4}$allyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatom selected from oxygen, sulfur or $NR_{12}$;

m is 0 or an integer of 1 or 2;

n is 0 or an integer of 1 or 2;

$R_3$ and $R_4$ are independently $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$;

$R_5$ and $R_6$ are each independently selected from hydrogen or optionally substituted $C_{1-4}$alkyl, optionally substituted aryl or optionally substituted aryl-$C_{1-4}$alkyl, or together with the nitrogen which they are attached form a heterocyclic ring of 5 to 7 members which ring optionally contains an additional heteroatom selected from oxygen, sulfur or $NR_9$;

Z is oxygen or sulfur;

$R_7$ is $C_{1-10}$ alkyl, $C_{3-7}$ cycloalkyl, aryl, arylalkyl, heterocyclyl, heterocyclyl-$C_{1-10}$alkyl, heteroaryl or heteroarylalkyl; wherein all of these moieties may be optionally substitued;

$R_8$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl; wherein all of these moieties may be optionally substitued;

$R_9$ is hydrogen, —$C(Z)R_8$ or optionally substituted $C_{1-10}$ alkyl, $S(O)_2 R_7$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, cyano, $C_{1-4}$ alkyl, $C_{3-7}$ cycloalkyl or aryl;

$R_{12}$ is $R_{10}$ or $C(Z)$—$C_{1-4}$ alkyl;

$R_{13}$ and $R_{14}$ is each independently selected from hydrogen or $C_{1-4}$ alkyl or $R_{13}$ and $R_{14}$ together with the nitrogen to which they are attached form a heterocyclic ring of 5 to 7 members which ring optionally contains an additional heteroatom selected from oxygen, sulfur or $NR_{17}$;

$R_{15}$ is hydrogen, $C_{1-4}$alkyl, $C_{2-4}$ alkenyl, $C_{2-4}$ alkynyl or $NR_{13}R_{14}$, provided that the moiety —$SR_{15}$ is not —$SNR_{13}R_{14}$ and the moiety —$S(O)R_{15}$ is not —$SOH$;

$R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{17}$ is hydrogen of C(Z)—$C_{1-4}$ alkyl;

$R_{23}$ is $C_{1-4}$ alkyl, halo-substituted-$C_{1-4}$ alkyl, or $C_{3-5}$ cycloalkyl;

$R_{36}$ is hydrogen or $R_{23}$;

or a pharmaceutically acceptable salt thereof.

Suitable heteroaryl moieties for $R_1$ and $R_2$ in Formula (II) are those as defined above for Formula (I), as are the remaining substituent groups, but for the $R_3$ and $R_4$ variables defined below.

Suitably, $R_3$ and $R_4$ are $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the aryl, arylalkyl, heteroaryl, heteroaryl alkyl, heterocyclic and heterocyclic alkyl moieties of $R_7$, $R_8$, $R_{10}$, $R_{11}$ may be optionally substituted as defined herein. More preferably, $R_3$ and $R_4$ are $NR_5R_6$ and $R_5$ and $R_6$ are independently hydrogen or $C_{1-4}$ alkyl.

In a preferred subgenus of compounds of formula (II), $R_1$ is 4-pyridyl, 2-alkyl4-pyridyl, 2-$NR_{10}R_{20}$-4-pyridyl, 4-pyrimidinyl, 2-alkyl-4-pyrimidinyl, 2-$NR_{10}R_{20}$-4-pyrimidinyl, or 4-quinolyl; $R_2$ is an optionally substituted phenyl group. More preferably $R_2$ is phenyl or phenyl substituted by fluoro, chloro, $C_{1-4}$ alkoxy, $S(O)_mC_{1-4}$ alkyl, methanesulfonamido or acetamido.

In yet another embodiment of the present invention are the novel compounds of Formula (III):

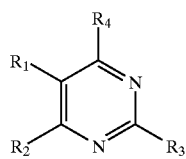

(III)

wherein:

$R_1$ is 4-pyridyl, 4-pyrimidinyl, 4-quinazolinyl, 4-quinolyl, or 6-isoquinolinyl, which rings are optionally substituted with one or two substituents, each of which is independently selected from Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, amino, mono and di-$C_{1-6}$ alkyl substituted amino, or $N(R_{10})C(O)R_b$;

Y is $X_1$—$R_a$;

$X_1$ is oxygen or sulfur;

$R_a$ is $C_{1-6}$aryl, aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ akyl, wherein each of these moieties may be optionally substituted;

$R_2$ is an optionally substituted aryl or optionally substituted heteroaryl group, provided that both $R_1$ and $R_2$ are not the same heteroaryl group; wherein when one $R_2$ is an optionally substituted aryl ring, the ring is substituted by one or two substituents, each of which is independently selected, and, which, for a 4-phenyl, 4-naphth-1-yl or 5-naphth-2-yl substituent, is halo, cyano, —C(Z)$NR_{13}R_{14}$, —C(Z)$OR_{23}$, —(CR$_{11}$OR$_{20}$)$_n$COR$_{36}$, —SR$_{15}$, —S(O)R$_{15}$, —OR$_{36}$, halo-substituted-$C_{1-4}$ alkyl, $C_{1-4}$ alkyl, —ZC(Z)$R_{36}$, —$NR_{10}C(Z)R_{23}$, or —(CR$_{10}$R$_{20}$)$_n$ $NR_{10}R_{20}$ and which, for other positions of substitution, is halo, cyano, —C(Z)$NR_{16}R_{26}$, —C(Z)OR$_8$, —(CR$_{10}$R$_{20}$)$_n$ COR$_8$, —S(O)$_m$R$_8$, —OR$_8$, halo-substituted-$C_{1-4}$ alkyl, —$C_{1-4}$ alkyl, —(CR$_{10}$R$_{20}$)$_n$ $NR_{10}C(Z)R_8$, —NHS(O)$_m$R$_7$, —NHS(O)$_m$NR$_{13}$R$_{14}$, —NR$_7$S(O)$_m$R$_7$, —NR$_7$S(O)$_{m'}$NR$_{13}$R$_{14}$, —ZC(Z)R$_8$ or —(CR$_{10}$R$_{20}$)$_n$ $NR_{16}R_{26}$; and when $R_2$ is an optionally substituted heteroaryl group, the substituent groups include one or two substituents each of which is independently selected from $C_{1-4}$ alkyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatorn selected from oxygen, sulfur or $NR_{12}$;

m is 0 or an integer of 1 or 2;

m' is an integer of 1 or 2;

m" is an integer having a value of 1 to 10;

n is 0 or an integer of 1 or 2;

n' is 0 or an integer having a value of 1 to 10;

n" is an integer having a value of 1 to 10

$R_3$ is hydrogen, $C_{1-10}$ alkyl, halosubstituted $C_{1-10}$ alkyl, —(CR$_{10}$R$_{20}$)$_n$·Q-(Y$_1$)$_t$, —(CR$_{10}$R$_{20}$)$_{n'}$ (Y$_2$)$_p$, —(CR$_{10}$R$_{20}$)$_{n''}$(Y$_3$)$_p$, or —(CR$_{10}$R$_{20}$)$_{m''}$ (Y$_4$)$_p$;

p is 0 or an integer of 1 or 2 t is an integer of 1, 2, or 3;

Q is an aryl or heteroaryl group;

$Y_1$ is independendy selected from hydrogen, halogen, $C_{1-5}$ alkyl, halo-substituted $C_{1-5}$ alkyl, —(CR$_{10}$R$_{20}$)$_{n'}$ (Y$_2$)$_p$, —(CR$_{10}$R$_{20}$)$_{n''}$ (Y$_3$)$_p$, or —(CR$_{10}$R$_{20}$)$_{m''}$ (Y$_4$)$_p$;

$Y_2$ is halogen, —OR$_8$, —S(O)$_{m'}$ R$_{18}$, —SR$_8$, —S(O)$_{m'}$ OR$_8$, —S(O)$_m$NR$_8$R$_9$, or —O(CR$_{10}$R$_{20}$)$_n$NR$_8$R$_9$, —ZC(O)R$_8$, or —OC(Z)NR$_8$R$_9$;

$Y_3$ is —NR$_8$R$_9$, —NR$_{10}$C(Z)R$_8$, —NR$_{10}$C(Z)NR$_8$R$_9$, —NR$_{10}$S(O)$_m$R$_{18}$, —N(OR$_{21}$)C(Z)NR$_8$R$_9$, —N(OR$_{21}$)C(Z)R$_8$, —NR$_{10}$C(=NR$_{11}$)SR$_{18}$, —NR$_{10}$C(=NR$_{11}$)NR$_8$R$_9$, —NR$_{10}$C(=CR$_{14}$R$_{24}$)SR$_{18}$, —NR$_{10}$C(=C(R$_{24}$)$_2$)NR$_8$R$_9$, —NR$_{10}$C(O)C(O)NR$_8$R$_9$, —NR$_{10}$C(O)C(O)OR$_{10}$, —NR$_{10}$S(O)$_m$CF$_3$, or —NR$_{10}$C(Z)OR$_{10}$;

$Y_4$ is —C(O)R$_8$, —CO$_2$R$_8$, —CO$_2$(CR$_{10}$R$_{20}$)$_{m''}$ CONR$_8$R$_9$, —CN, —C(Z)NR$_8$R$_9$, —C(Z)NR$_8$OR$_9$, —C(=NOR$_{21}$)R$_8$, —C(=NR$_{19}$)NR$_8$R$_9$, —C(=NOR$_{19}$)NR$_8$R$_9$, —C(=NR$_{19}$)ZR$_{18}$, —NR$_{10}$S(O)$_m$CF$_3$, or —NR$_{10}$C(Z)OR$_{10}$O;

$R_4$ is hydrogen, $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the aryl, arylalkyl, heteroaryl, heteroaryl alkyl, heterocyclic and heterocyclic alkyl moieties of $R_7$, and $R_8$ may be optionally substituted;

$R_5$ and $R_6$ are each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{17}$;

Z is oxygen or sulfur;

$R_7$ is $C_{1-10}$ alkyl, $C_{3-7}$ cycloalkyl, aryl, arylalkyl, heterocyclyl, heterocyclyl-$C_{1-10}$ alkyl, heteroaryl or heteroarylalkyl;

$R_8$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{17}$;

$R_{10}$ and $R_{20}$ is each independently selected from hydrogen or $C_{1-4}$ alkyl; $R_{1-11}$ is hydrogen, cyano, $C_{1-4}$ alkyl, $C_{3-7}$ cycloalkyl or aryl; $R_{12}$ is $R_{10}$ or $C(Z)$—$C_{1-4}$ alkyl;

$R_{13}$ and $R_{14}$ is each independently selected from hydrogen or $C_{1-4}$ alkyl or $R_{13}$ and $R_{14}$ together with the nitrogen to which they are attached form a heterocyclic ring of 5 to 7 members which ring optionally contains an additional heteroatom selected from oxygen, sulfur or $NR_{22}$;

$R_{15}$ is hydrogen, $C_{1-4}$ alkyl, $C_{2-4}$ alkenyl, $C_{2-4}$ alkynyl or $NR_{13}R_{14}$, provided that the moiety —$SR_{15}$ is not —$SNR_{13}R_{14}$ and the moiety —$S(O)R_{15}$ is not —$SOH$;

$R_{16}$ and $R_{26}$ is each independently selected from hydrogen or optionally substituted $C_{1-4}$alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{17}$;

$R_{17}$ is hydrogen, —$C(Z)R_8$ or optionally substituted $C_{1-10}$ alkyl, $S(O)_2R_7$, optionally substituted aryl or optionally substituted aryl-$C_{1-4}$ alkyl;

$R_{18}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl; $R_{19}$ is hydrogen, $C_{1-10}$ alkyl, cycloalkyl, heterocyclyl, aryl, arylalkyl, heteroaryl or heteroarylalkyl;

$R_{21}$ is hydrogen, a pharmaceutically acceptable cation, $C_{1-10}$ alkyl, $C_{3-7}$ cycloalkyl, aryl, aryl $C_{1-4}$alkyl, heteroaryl, heteroarylalkyl, heterocyclyl, aroyl, or $C_{1-10}$ alkanoyl;

$R_{22}$ is $R_{10}$ or $C(Z)$—$C_{1-4}$ alkyl;

$R_{23}$ is $C_{1-4}$ alkyl, halo-substituted-$C_{1-4}$ alkyl, or $C_{3-5}$ cycloalkyl;

$R_{24}$ is independently selected from hydrogen, alkyl, nitro or cyano;

$R_{36}$ is hydrogen or $R_{23}$;

or a pharmaceutically acceptable salt thereof.

Suitable heteroaryl moieties for $R_1$ and $R_2$ in Formula (III) are the same as defined above for Formula (1), as are the remaining substituent groups, but for $R_3$ and $R_4$ variables defined below.

Suitably, $R_4$ is $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the aryl, arylalkyl, heteroaryl, heteroaryl alkyl, heterocyclic and heterocyclic alkyl moieties of $R_5$, $R_6$, $R_7$, $R_8$, $R_{10}$, and $R_{11}$ may be optionally substituted as herein defined. More preferably $R_4$ is $NR_5R_6$ and $R_5$ and $R_6$ arehydrogen or $C_{1-4}$ alkyl.

Suitably, $R_3$ is hydrogen, $C_{1-10}$ alkyl, halosubstituted $C_{1-10}$ alkyl, —$(CR_{10}R_{20})_{n'}$ Q-$(Y_1)_t$, —$(CR_{10}R_{20})_{n'}$ $(Y_2)_p$, —$(CR_{10}R_{20})_{n''}(Y_3)_p$, or —$(CR_{10}R_{20})_{m''}(Y_4)_p$. Preferably when $R_3$ is —$(CR_{10}R_{20})_{n'}Q$-$(Y_1)_t$ then Q is aryl, and t is 1. Suitably $R_3$ is —$(CR_{10}R_{20})_{n''}(Y_3)_p$.

$Y_2$ is suitably halogen, —$OR_8$, —$S(O)_mR_{18}$, —$SR_8$, —$S(O)_{m'}OR_8$, —$S(O)_mNR_8R_9$, or —$O(CR_{10}R_{20})_nNR_8R_9$, —$ZC(O)R_8$, or —$OC(Z)NR_8R_9$.

$Y_3$ is suitably —$NR_8R_9$, —$NR_{10}C(Z)R_8$, —$NR_{10}C(Z)NR_8R_9$, —$NR_{10}S(O)_mR_{18}$, —$N(OR_{21})C(Z)NR_8R_9$, —$N(OR_{21})C(Z)R_8$, —$NR_{10}C(=NR_{11})SR_{18}$, —$NR_{10}C(=NR_{11})NR_8R_9$, —$NR_{10}C(=CR_{14}R_{24})SR_{18}$, —$NR_{10}C(=C(R_{24})_2)NR_8R_9$, —$NR_{10}C(O)C(O)NR_8R_9$, —$NR_{10}C(O)C(O)OR_{10}$, —$NR_{10}S(O)_mCF_3$, or —$NR_{10}C(Z)OR_{10}$.

$Y_4$ is suitably —$C(O)R_8$, —$CO_2R_8$, —$CO_2(CR_{10}R_{20})_{m''}CONR_8R_9$, —$CN$, —$C(Z)NR_8R_9$, —$C(Z)NR_8OR_9$, —$C(=NOR_{21})R_8$, —$C(=NR_{19})NR_8R_9$, —$C(=NOR_{19})NR_8R_9$, —$C(=NR_{19})ZR_{18}$, —$NR_{10}S(O)_mCF_3$, or —$NR_{10}C(Z)OR_{10}$.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $C(Z)NR_8OR_9$, $NR_{10}C(Z)NR_8R_9$, or $OR_8$.

As used herein, for all formulas, "optionally substituted" unless specified, refers to such groups as halogen, halo $C_{1-6}$ alkyl, $C_{1-6}$ alkyl, hydroxyl, hydroxyl substituted $C_{1-6}$ alkyl, $C_{1-6}$ alkoxy, $S(O)_mC_{1-6}$ alkyl, amino, a mono & di $C_{1-6}$alkyl substituted amino, $C_{3-7}$ cycloalkyl, aryl or arylalkyl wherein the cycloalkyl and aryl moieties may be optionally substituted by halogen, hydroxyl, alkoxy, $S(O)_mC_{1-6}$ alkyl, amino, a mono & di-$C_{1-6}$alkyl substituted amino, $C_{1-6}$ alkyl, or halo $C_{1-6}$ akyl.

Suitable pharmaceutically acceptable salts are well known to those skilled in the art and include basic salts of inorganic and organic acids, such as hydrochloric acid, hydrobromc acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo;

"$C_{1-10}$ alkyl" or "akyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

The term "cycloalkyl" is used herein to mean cyclic radicals, preferably of 3 to 7 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy")—a 5–10 membered aromatic ring system in which one or more rings contain one or more heteroatoms selected from the group consisting of N, O or S, such as, but not limited, to pyrrole, thiophene, quinoline, isoquinoline, pyridine, pyrimidine, oxazole, thiazole, thiadiazole, triazole, imidazole, or benzimnidazole;

"heterocyclic" (on its own or in any combination, such as "heterocyclylalkyl")—a saturated or wholly or partially unsaturated 4–10 membered ring system in which one or more rings contain one or more heteroatoms selected from the group consisting of N, O, or S; such as, but not limited to, pyrrolidine, piperidine, piperazine, morpholine, imidazolidine or pyrazolidine;

The term "aralkyl" or "heteroylalkyl" or "heterocyclicalkyl" is used herein to mean $C_{1-4}$ alkyl as defined above unless otherwise indicated "sulfinyl"—the oxide S(O) of the corresponding sulfide while the term "thio" refers to the sulfide.

The compounds of the present invention may contain one or more asymmetric carbon atoms and may exist in racenic and optically active forms. All of these compounds are included within the scope of the present invention.

Compounds of Formula (I) may be readily prepared using procedures well known to those of skill in the art and may be prepared by analogous methods to those indicated herein below.

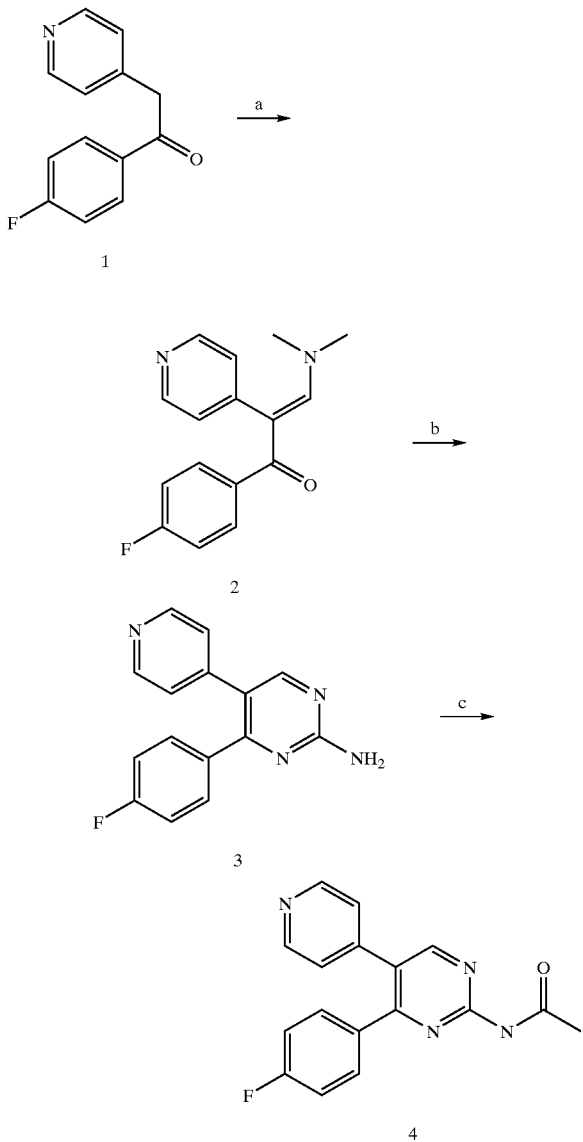

Scheme I

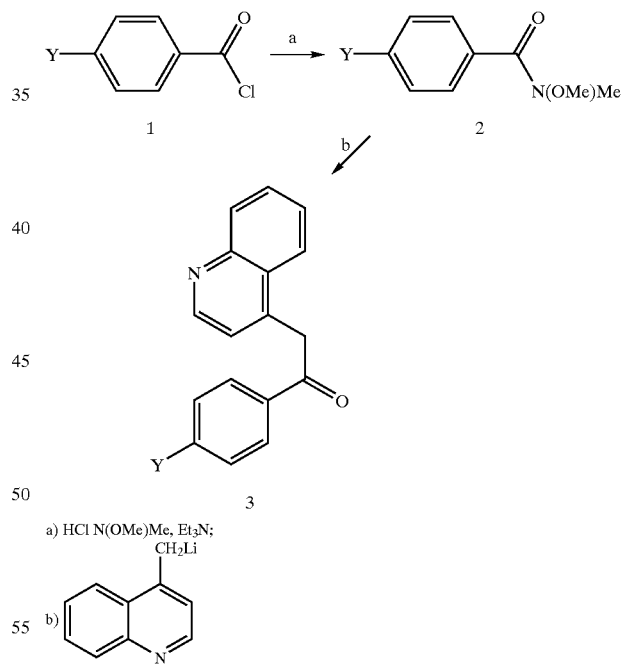

a) $(CH_3O)_2CHN(CH_3)_2$;
b) $H_2NC(=NH)NH_2$
   HCl, NaOEt, EtOH;
c) $Ac_2O$

While the illustration in Schemes I and II are for the preparation of a particular compound of Formula (I) (i.e., Scheme I, $R_1$=-pyridyl, $R_2$=4-fluorophenyl and $R_3$=acetamide), generalization of the synthesis to groups claimed as $R_1$ and $R_2$ and $R_3$ herein can be achieved by starting with the appropriate acetophenones, preparation of which are disclosed in PCT/US93/00674, now U.S. Pat. No. 5,686,455, notably Scheme I, whose disclosure is herein incorporated by reference. Conversion of the appropriate acetophenone to the corresponding enamine 2 is outlined in EP 0 531 901 A2 whose disclosure is incorporated by reference herein. Treatment of 2 with a guanidine, or a mono- or di alkyl guanidine, affords pynmidine 3 where $R_3$ is equal to a primary, secondary or tertiary amino group, respectively. The desired guanidines are either commercially available or can be prepared by the procedure outlined in Oxley, P. et al., *J. Chem. Soc.*, (1951), 1252 whose disclosure is incorporated by reference herein. Pyriridine 3 can be converted to additional compounds of Formula (I) wherein $R_3$ is the corresponding sulphonamide, amide, urea, guanidine or urethane by using techniques well known to those of skill in the art of the appropriate acylating agents, such as sulfonyl chlorides, acid chlorides, isocyanates, dicyanamides and chloroformates, respectively.

Scheme II a) HCl N(OMe)Me, $Et_3N$;
   $CH_2Li$
b)

The appropriately substituted acetephone, 3-Scheme-II, is prepared by adding the anion of 4-methyl-quinoline (step b), which is prepared by treatment thereof with an alyl lithium derivative, such as n-butyl lithium, to an N-alkyl-O-alkoxybenzamide. Suitably, the other $R_1$ moieties may be prepared in an analogous manner. Alternatively, the anion may be condensed with a benzaldehyde, to give an alcohol which is then oxidized to the ketone 3.

Compounds of Formula (II) are also pyrimidine derivatives which may be readily prepared using procedures well known to those of skill in the art and may be prepared by analogous methods to those indicated herein below.

Scheme III

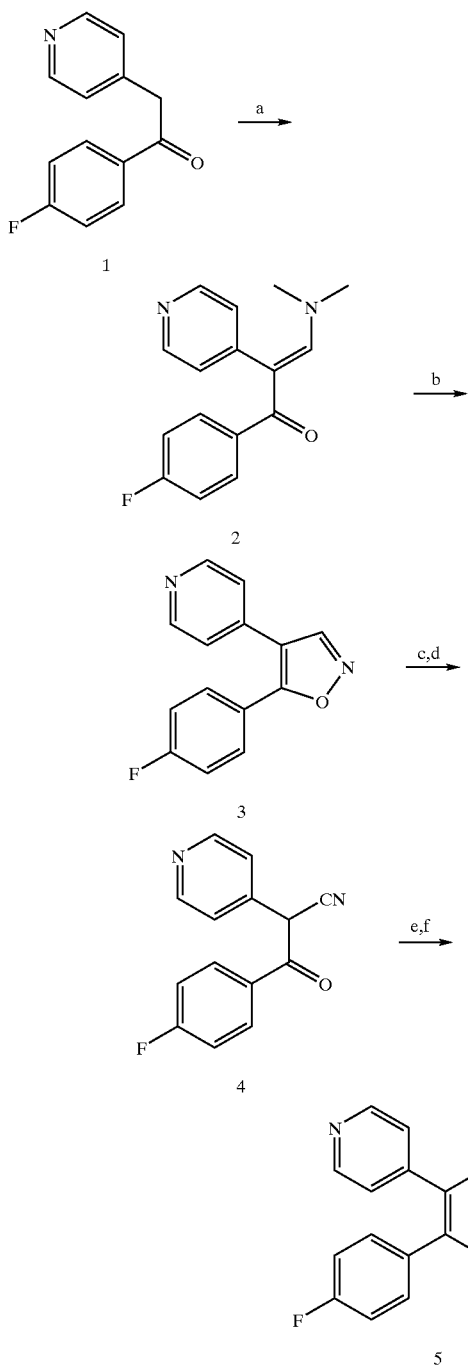

a) (CH$_3$O)$_2$CHN(CH$_3$)$_2$;
b) H$_2$NOH·HCl;
c) NaOH;
d) HCl;
e) TBDMSt$_2$O, CH$_2$Cl$_2$;
f) H$_2$NC(═NH)NH$_2$·HCl,EtOH

While the illustration in Schemes III and IV are for the preparation of a particular compound of Formula (II) (i.e., Scheme IV, R$_1$=-pyridyl, R$_2$=4-fluorophenyl, R$_4$=amino and R$_3$=hydrogen), generalization of the synthesis to groups claimed as R$_1$ and R$_2$ and R$_3$ herein can be achieved by starting with the appropriate acetophenones, preparation of which are disclosed in PCT/US93100674, noteably Scheme IV, whose disclosure is incorporated by reference herein. Conversion to the corresponding enamine 2, isoxazole 3 and propanenitrile 4 is outlined in EP 0 531 901 A2 whose disclosure is incorporated by reference herein. Conversion of propanenitrile 4 is facilitated by formation of an enol ether derivative (e.g., a silyl enol ether). Subsequent treatment with guanidine, or a mono- or dialkyl guanidine, affords pyrimidine 5 where R$_3$ is equal to a primary, secondary or tertiary amino group, respectively, and R$_4$ is NH$_2$. The desired substituted guanidines (resulting in R$_3$) are either commercially available, or can be prepared by the procedure outlined in Oxley, P. et al., *J. Chem. Soc.*, (1951), 1252. The R$_3$ group of a pyrimidine 5 may if needed, be protected prior to derivatization, of the amino group (R$_4$) such as noted below. Alternatively, the R$_3$ moiety may also be de-protected and derivatized as well. Suitable derivitazation and protection techniques are well known by one of skill in the art. For instance, when R$_3$ is a dialkyl amine, R$_4$ can be converted to the corresponding sulphonamide, amide, urea, guanidine or urethane by using the appropriate acylating agents such as sulfonyt chlorides, acid chlorides, isocyanates, dicyanamides and chloroformates, respectively. When R$_3$ is a primary amnine, R$_3$ and R$_4$ can be converted to the bis-sulphonamides, bisamides, bisureas, bis-guanidines or bisurethanes by using the appropriate acylating agents such as those listed above, with appropriate separation techniques if need be.

Scheme IV

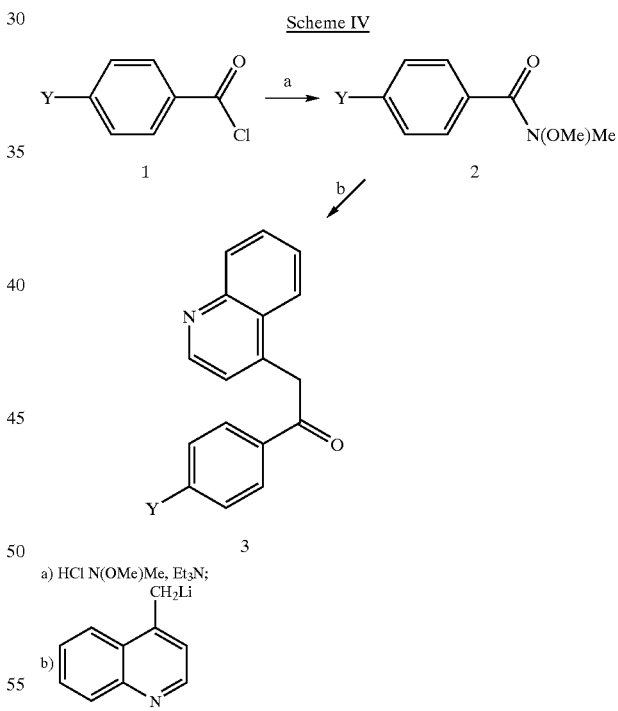

a) HCl N(OMe)Me, Et$_3$N;
CH$_2$Li b)

The appropriately substituted acetaphenone, 3 of scheme 4 is prepared by adding the anion of 4-methyl-quinoline (step b), which is prepared by treatment thereof with an alkyl lithium derivative, such as n-butyl lithium, to an N-alyl-O-allkoxybenzamide. Suitably, the other R$_1$ moieties may be prepared in an analagous manner. Alternatively, the anion may be condensed with a benzaldehyde, to give an alcohol which is then oxidised to the ketone 3.

Compounds of Formula (III) are pyrimidine derivatives which may be readily prepared using procedures well known to those of skill in the art and may be prepared by analogous methods to those indicated below.

Scheme V

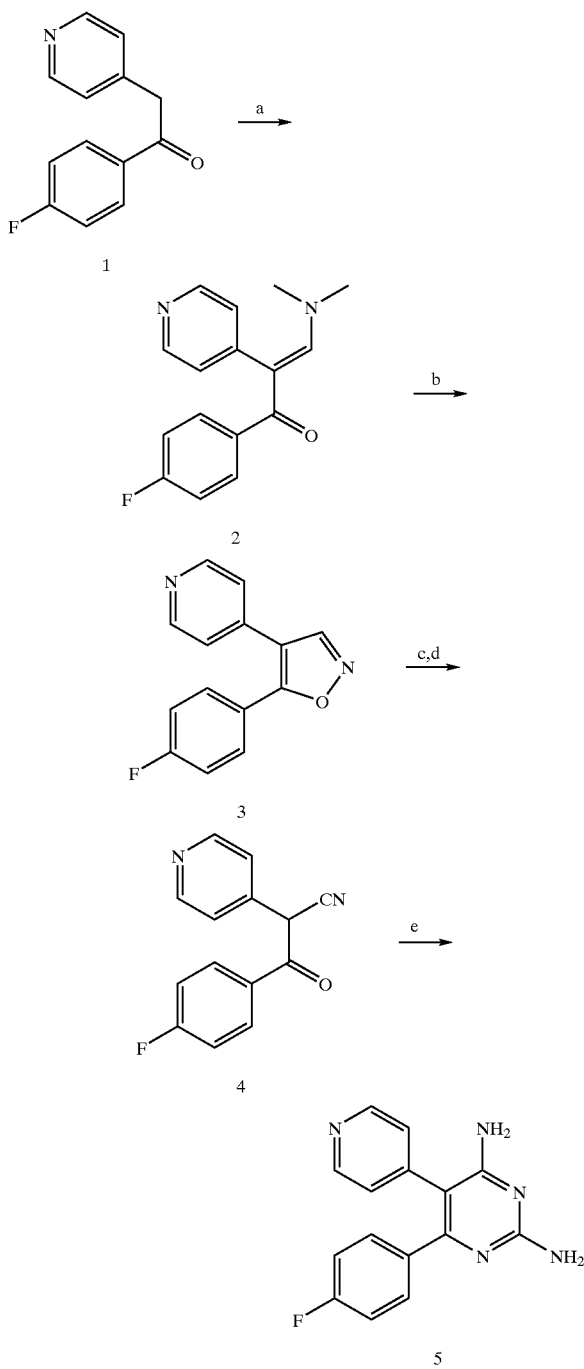

a) (CH$_3$O)$_2$CHN(CH$_3$)$_2$;
b) H$_2$NOH HCl, EtOH
c) NaOH;
d) HCl;
e) HCONH$_2$, NH$_3$

While the illustration in Schemes V and VI are for the preparation of a particular compound of Formula (III) (i.e., Scheme I, R$_1$=-pyridyl, R$_2$=4-fluorophenyl, R$_4$=amino and R$_3$=hydrogen), generalization of the synthesis to groups claimed as R$_1$, R$_2$ and R$_3$ herein can be achieved by starting with the appropriate acetophenones, preparation of which are disclosed in PCT/US93/00674, noteably Scheme VI, whose disclosure is herein incorporated by reference. Conversion to the corresponding enamine 2, isoxazole 3 and propanenitrile 4 is outlined in EP 0 531 901 A2, whose disclosure is incorporated by reference herein. Subsequent treatment of 4 with the appropriately substituted amidine gives a substituted R$_3$-4-amino pyrimidine of Formula (III). Alternatively, appropriately substituted amidines may be used in step (e) to produce directly compounds of Formula (III) which may then be used, as necessary, as intermediates to produce further compounds of Fonnula (III) through deriviatization. Appropriately substituted amidines may be made using the procedures such as those taught in Garigipati, R. S., Tet. Lett., (1990), 31 (14), 1969 whose disclosure is incorporated by reference herein. Pyrimidine 5 can be converted to to additional compounds of Formula (III) wherein R$_4$ is the corresponding sulphonamide, amide, urea, guanidine or urethane by using the appropriate acylating agents such as sulfonyl chlorides. isocyanates, dicyanarnides and chloroformates, respectively. While it is recognized that in the Scheme I the R$_4$ amino group is unsubstituted, (R$_5$ and R$_6$=hydrogen) the amino agroup may also be suitably converted to the mono- or di-alkyl derivative by one of skill in the art by appropriate and well known techniques.

Scheme VI

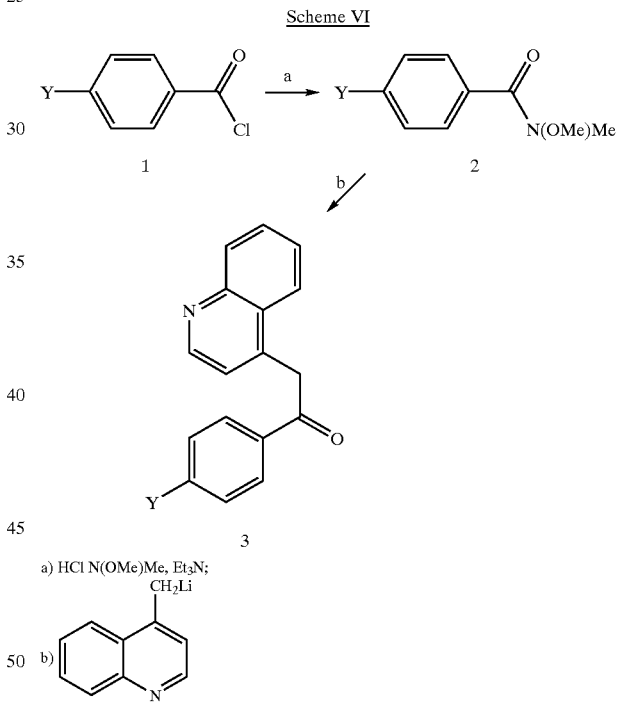

a) HCl N(OMe)Me, Et$_3$N;
CH$_2$Li b)

The appropriately substituted acetophone, 3-Scheme-6, is prepared by adding the anion of 4-methyl-quinoline (step b), which is prepared by treatment thereof with an alkyl lithium derivative, such as n-butyl lithium, to an N-alkyl-O-alkoxybenzamide. Suitably, the other R$_1$ moieties may be prepared in an analagous manner. Alternatively, the anion may be condensed with a benzaldehyde. to give an alcohol which is then oxidised to the ketone 3.

Suitable protecting groups for use in the present invention, are well known in the art and described in many references, for instance, Protecting Groups in Organic Synthesis, Greene T W, Wiley-Interscience, New York, 1981.

Pharmaceutically acid addition salts of compounds of formula (I), (II) or (III) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

2-Amino-4-(4-fluorophenyl)-5-(4-pyridyi)pyrimidine (a) 3-Dimethylamiino-1-(4-fluorophenyl)-2-(pyridin-4-yl)-2-propen-1-one—The title compound was prepared following the procedure of Marusawa, H. et al. EP 0 531 901 A2.

(b) 2-Amino-4-(4-fluoropbenyl)-5-(4-pyridyl)pyrimkine— The title compound was prepared following the procedure of Bennett, G. et al., *J. Med Chem.*, 1978, 21(7), 623 except using 3-dimethylamino-1-(4-fluorophenyl)-2-(pyridin-4-yl)-2-propen-1-one: ESMS (m/z): 267.0 (M$^+$+H).

(c) 2-Acetamido-4-(4-fluorophenyl)-5-(4-pyridyl) pyrimidine A mixture of 2-amino-4-(4fluorophenyl)-5-(4-pyridyl)pyrimidine in acetic anhydride is stirred at room temperature. After 72 h the mixture is poured into H$_2$O and neutralized with conc. NH$_4$OH. The resulting precipitate is filtered and washed with H$_2$O. Purification by column chromatography, followed by recrystallization, affords the title compound.

Example 2

2,4-Diamino-5-(4-fluorophenyl)-6-(4-pyridyl)pyrimidine (a) 3-Dimethylamino-1-(4-fluorophenyl)-2-pyridin-4-yl)-2-propene-1-one—The title compound is prepared following the procedure of Marusawa, H. et at. EP 0 531 901 A2.

(b) 5-(4-Fluorophenyl)-4-(pyrldin-4-yl)isoxazole—The title compound is prepared following the procedure of Marusawa, H. et aL EP 0 531 901 A2.

(c) 3-(4-Fluorophenyl)-3-oxo-2-(pyridin-4yl) propanenitrile—The title compound is prepared following the procedure of Marusawa, H. et al. EP 0 531 901 A2.

(d) 2,4-Diamino-5-(4-fluorophenyl)-6-(4-pyridyl) pyrimndine—The title compound is prepared following the procedure of Russell, P. B. et al. *J. Amer. Chem Soc.*, 1951, 73, 3763 except using 3-(4-fluorophenyl)-3-oxo-2-(pyridin-4-yl)propanenitrile.

Example 3

4-Amino-6-(4-fluorophenyl)-5-(4-pyridyl)pyrimidine (a) 3-Dimethylamino-1-(4-fluorophenyl)-2-(pyridin-4-yl)-2-propen-1-one—The title compound is prepared following the procedure of Marusawa, H. et al. EP 0 531 901 A2.

(b) S-(4-Fluorophenyl)-4-(pyridin-4-yl)isoxazole—The tide compound is prepared following the procedure of Marusawa, H. et al. EP 0 531 901 A2.

(c) 3-(4-Fluorophenyl)-3-oxo-2-(yridin-4-yl) propanenitrble—The title compound is prepared following the procedure of Marusawa, H. et al. EP 0 531 901 A2.

(d) 4-Amino-6-(4-fluorophenyl)-5-(4-pyridyl)pyrimidine— The title compound is prepared following the procedure of Nagamatsu, T. et al. *Synthesis*, 1991, 303 except using 3-(4-fluorophenyl)-3-oxo-2-(pyridinA4yl)propanenitrile.

Methods of Treatment

The compounds of Formula (I), (II), or (III) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as, but not limited to monocytes and/or macrophages.

For simplicity, in the method of treatment section herein, the term "compounds of Formula (I)" should be recognized to mean compounds of Formula (I), (II) or (III).

Compounds of formula (1) are capable of inhibiting proinflammatory cytokines, such as IL-1, IL-6, IL-8 and TNF and are therefore of use in therapy. IL-1, IL-8 and TNF affect a wide variety of cells and tissues and these cytokines, as well as other leukocyte-derived cytokines, are important and critical inflammatory mediators of a wide variety of disease states and conditions. The inhibition of these pro inflammatory cytokines is of benefit in controlling, reducing and alleviating many of these disease states.

Accordingly, the present invention provides a method of treating a cytokine-mediated disease which comprises administering an effective cytokineinterfering amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said manmmal an effective amount of a compound of formula (I) or a pharmaceutically acceptable salt thereof.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic 8 cells and Alzheimefs disease.

In a further aspect, this invention relates to a method of inhibiting the production of TNF in a mammal in need thereof which comprises administering to said mammal an effective amount of a compound of formula (I) or a pharmaceutically acceptable salt thereof Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distrmss syndrome, cerebral malaria, chronic pulmonary inflammatory disease, silicosis, pulmonary sarcoisosis, bone resorption diseases, such as osteoporosis, reperfiision injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo.

The viruses contemplated for treatment herein are those that produce TNF as a result of infection, or those which are sensitive to inhibition, such as by decreased replication, directly or indirectly, by the TNF inhibiting-compounds of formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

Compounds of formula (I) may also be used in association with the veterinary treatment of mnamnals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Another aspect of the present invention relates to a method of inhibiting the production of IL-8 (Interleukin-8, NAP) in a mammal in need thereof which comprises administering to said mammal an effective amount of a compound of formula (1) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of IL-1, IL-8 or TNF mRNA above basal levels in cells or tissues in which IL-1, IL-8 or INF, respectively, is produced.

The discovery that the compounds of formula (I) are inhibitors of cytokines, specifically IL-1, IL-8 and TNF is based upon the effects of the compounds of formulas (I) on the production of the IL-1, IL-8 and TNF in in vitro assays which are described herein.

As used herein, the term "inhibiting the production of IL-1 (IL-8 or TNF)" refers to:

a) a decrease of excessive in vivo levels of the cytokine (IL-1, IL-8 or TNF) in a human to normal or subnormal levels by inhibition of the in vivo release of the cytokine by all cells, including but not limited to monocytes or macrophages;

b) a down regulation, at the genomic level, of excessive in vivo levels of the cytokine (IL-1, IL-8 or TNF) in a human to normal or sub-normal levels;

c) a down regulation, by inhibition of the direct synthesis of the cytokine (IL-1, IL-8 or TNF) as a postranslational event; or d) a down regulation, at the translational level, of excessive in vivo levels of the cytokine (IL-1, IL-8 or TNF) in a human to normal or subnormal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-1).

As used herein, the term "cytokine interfering" or "cytokine suppressive amount" refers to an effective amount of a compound of formula (I) which will cause a decrease in the in vivo levels of the cytokine to normal or subnormal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIVinfected human" is a cytokine which is implicated in (a) the initiation and/or maintenance of T cell activation and/or activated T cell-mediated HIV gene expression and/or replication and/or (b) any cytokine-mcdiated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

Compounds of Formula (I) are capable of inhibiting inducible proinflamnatory proteins, such as COX-2, also referred to by many other names such as prostaglandin endoperoxide synthase-2 (PGHS-2) and are therefore of use in therapy. These proinflamnratory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and cntical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these proinflanmmatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I), (II), or (III) or a pharmaceutically acceptable salt thereof. The present invention also provides for a method of prophylaxis treatment in a human, or other mammal, by inhibition of the synthesis of the COX-2 enzyme.

A new member of the MAP kinase family, alternatively termed CSBP, p38, or RK, has been identified independently by several laboratories recently. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors of the present invention may be determined to be potent and selective inhibitors of CSBP/p38/RK kinase activity by the assay as described herein. These inhibitors are of aid in detemining the signaling pathways involvement in inflammnatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for antiinflamrnmatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). *B Ann. N. Y. Acad. Sci.* 696, 149–170.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation ofan oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to about 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily.

The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated. the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

The invention will now be described by reference to the following examples which are merely illustrative and are not to be construed as a limitation of the scope of the present invention.

BIOLOGICAL EXAMPLES

The cytokineinhibiting effects of compounds of the present invention are determined by the following in vitro assays:

Interleukin 1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1\times10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture super-natants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL4) to secrete IL-2, in concert with A23187 ionophore) or the method of Lee et al., J. Immuno Therapy, 6 (1), 1–12 (1990) (ELISA assay).

Tumor Necrosis Factor (TNF)

Human peripheral blood monocytes are isolated and purified from either blood bank buffy coats or plateletpheresis residues, according to the procedure of Colotta, R. et al., J Immunol, 132(2), 936 (1984). The monocytes are plated at a density of $1\times10^6$ cells/tnl medium/well in 24-well multidishes. The cells are allowed to adhere for 1 hour after which time the supernatant is aspirated and fresh medium (1 ml, RPMI-1640, Whitaker Biomedical Products, Whitaker, Calif.) containing 1% fetal calf serum plus penicillin and streptomycin (10 units/ml) added. The cells are incubated for 45 minutes in the presence or absence of a test compound at 1 nM–10 mM dose ranges (compounds were solubilized in dimethyl sulfoxidelethanol, such that the fmal solvent concentration in the culture medium is 0.5% dimethyl sulfoxide/0.5% ethanol). Bacterial lipopoly-saccharide (*E. coli* 055:B5 [LPS] from Sigma Chemicals Co.) is then added (100 ng/ml in 10 ml phosphate buffered saline) and cultures incubated for 16–18 hours at 37° C. in a 5% $CO_2$ incubator. At the end of the incubation period, culture supernatants are removed from the cells, centrifuged at 3000 rpm to remove cell debris. The supernatant is then assayed for TNF activity using either a radio-immuno or an ELISA assay, as described in WO 92/10190 and by Becker et al., J Immunol, 1991, 147, 4307.

In vivo TNF assay:

While the above indicated assay in an in vitro assay, the compounds of Formula (I), (II) or (III) may also be tested in an in vivo system such as described in:

(1) "Differentiation In Vivo of Classical Non—Steroidal Antiinflanmatory Drugs from Cytokine Suppressive Antiinflammatory Drugs and Other Pharmacological Classes Using Mouse Tumour Necrosis Factor Alpha Production", Griswold et al., *Drugs Under EXp. and Clinical Res.*, XIX (6), 243–248 (1993); or in (2) Boehm, et al., 1-substituted 4aryl-5-pyridinyliidazoles—a new class of cytbkine suppressive drugs with low 5-lipoxygenase and cyclooxygenase inhibitory potency. *Journal Of Medicinal Chemistry* 39, 3929–3937 (1996) whose disclosures are incorporated by reference herein in their entirety.

The IL-8 cytokineinhibiting effects of compounds of the present invention may be determined by the following in vitro assay.

Receptor Binding Assays:

[$^{125}$I] IL-8 (human recombinant) is obtained from Amersham Corp., Arlington Heights, Ill., with specific activity 2000 Ci/mmol. All other chemicals are of analytical grade. High levels of recombinant human IL-8 type α and β receptors are individually expressed in Chinese hamster ovary cells as described previously (Holmes. et al., *Science*, 1991, 253, 1278). The Chinese hamster ovary membranes are homogenized according to a previously described protocol (Haour, et al., *J Biol Chem.*, 249 pp 2195–2205 (1974)). Except that the homogenization buffer is changed to 10 mM Tris-HCL, 1 mM MgSO4, 0.5 mM EDTA (ethylenediaminetetra-acetic acid), 1 mMPMSF (c-toluenesulphonyl fluoride), 0.5 mg/L Leupeptin, pH 7.5. Membrane protein concentration is determined using Pierce Co. microassay kit using bovine serum albumin as a standard. All assays are performed in a 96-well micro plate format. Each reaction mixture containes $^{125}$I IL-8 (0.25 nM), 0.5 μg/mL of IL-8Ra or 1.0 μg/mL of IL-8Rb membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, the drug or compound of interest is added which has been pre-dissolved in DMSO so as to reach a final concentration of between 0.01 nM and 100 uM. The assay is initiated by addition of $^{125}$I-IL-8. After 1 hour at room temperature the plate is harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter is then dried and counted on the Betaplate liquid scintillation counter. The recombinant IL-8 Rα, or Type I, receptor is also referred to herein as the non-permissive receptor and the recombinant IL-8β, or Type II, receptor is referred to as the permissive receptor.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP 1 cells and a radiolabeled compound. Patent Application U.S. Ser. No. 08/123175 Lee et al., filed September 1993, Lee et al., PCT 94/10529 filed Sep. 16, 1994 and Lee et al., *Nature* 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/binding protein complex and compound capable of forming, enhancing or interfering with said complexes are detected.

CSBP Kinase Assay

This assay measures the CSBP-catalyzed transfer of $^{32}$P from [a-$^{32}$P]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Inidazoles: Inhibition of CSPB Kinase", BioOrgardc & Medicinal Chemistry, to be published 1996).

Kinase reactions (total volume 30 ul) contain: 25 mM Hepes buffer, pH 7.5; 10 mM MgCl$_2$; 170 uM ATP[1]; 10 uM Na ortho vanadate; 0.4 mM T669 peptide; and 20–80 ng of yeast-expressed purified CSBP2 (see Lee et al., Nature 300, n(72), 739–746 (December 1994)). Compounds (5 ul from [6X] stock[2]) are preincubated with the enzyme and peptide for 20 min on ice prior to starting the reactions with $^{32}$P/MgATP. Reactions are incubated at 30° C. for 10 miin and stopped by adding 10 ul of 0.3 M phosphoric acid. 32P-labeled peptide is separated on phosphocellulose (Watman, p81) filters by spotting 30 ul reaction mixture. Filters are washed 3 times with 75 mM phosphoric acid followed by 2 washes with H$_2$O, and counted for 32P.

[1] The Km of CSBP for ATP was determined to be 170 uM. Therefore, compounds screened at the Km value of ATP.

[2] Compounds are usually dissolved in DMSO and are diluted in 25 mM Hepes buffer to get final concentration of DMSO of 0.17%.

Prostogiandin Endoperoidde Synthase-2 (PGHS-2) Assay

The following assay describes a method for determining the inhibitory effects of compounds of Formula (V) on human PGHS-2 protein expression in LPS stimulated human monocytes. Method: Human peripheal blood monocytcs were isolated from buffy coats by centrifugation through Ficoll and Percoll gradients. Cells were seeded at 2×10$^6$/well in 24 well plates and allowed to adhere for 1 hour in RPM1 supplemented with 1% human AB serum, 20 mM L-glutarnine, Penicillin—Streptomycin and 10 mM HEPES. Compounds were added at various concentrations and incubated at 37° C. for 10 minutes. LPS was added at 50 ng/well (to induce enzyme expression) and incubated overnight at 37° C. The supernatant was removed and cells washed once in cold PBS. The cells were lysed in 100 μl of cold lysis buffer(50 mM Tris/HCl pH 7.5, 150 mM NaCl, 1% NP40, 0.5% sodium deoxycholate, 0.1% SDS, 300 ug/ml DNAse, 0.1% TRITON X-100, 1 mM PMSF, 1 mM leupeptin, 1 mM pepstatin). The lysate was centrifuged (10,000×g for 10 min. at 4° C.) to remove debris and the soluble fraction was subjected to SDS PAGE. analysis (12% gel). Protein separated on the gel were transferred onto nitrocellulose membrane by electrophoretic means for 2 hours at 60 volts. The membrane was pretreated for one hour in PBS/0.1% Tween 20 with 5% non-fat dry milk. After washing 3 times in PBS/Tween buffer, the membrane was incubated with a 1:2000 dilution of a monospecific antiserum to PGHS-2 or a 1:1000 dilution of an antiserum to PGHs-1 in PBS/Tween with 1% BSA for one hour with continuous shaking. The membrane was washed 3× in PBS/Tween and then incubated with a 1:3000 dilution of horseradish peroxidase conjugated donkey antiserum to rabbit Ig (Amersham) in PBS/Tween with 1% BSA for one hour with continuous shaking. The membrane was then washed 3× in PBS)Tween and the ECL immunodetection system (Amersham) was used to detect the level of expression of prostaglandin endoperoxide synthases-2. Results: The following compounds were tested and found to be active in this assay (i.e., inhibited LPS induced PGHS-2-protein expression in rank order potency similar to that for inhibiting cytokine production as noted in assays indicated): 4-(4-Fluorophenyl)-2-(4-methylsulfmylphenyl)-5-(4-pyiidyl) iridazole; 6-(4-Fluorophenyl)-2,3-dihydro-5-(4-pyridinyl) imidazo[2,1-b]thiazole; and Dexamethasone Several compounds were tested and found to be inactive (up to 10 uM): 2-(4-Methylsulfinylphenyl)-3-(4-pyridyl)-6,7-dihydro (5H)-pyrrolo[1,2-a]imidazolerolipram; phenidone and NDGA. None of the compounds tested was found to inhibit PGHS-1 or cPLA$_2$ protein levels in similar experiments.

TNF-α in Traumatic Brain Injury Assay

The present assay provides for examination of the expression of tumor necrosis factor mRNA in specific brain regions which follow experimentally induced lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization is performed and quantitated relative to an TNF-α positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (468%, p<0.05), LC (30%, p<0.01) and LA (32±3%, p<0.01) at 6 hr. which resolves by 24 hr. following injury. In the contalateral hemnisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA is observed in any of the 6 brain areas in either hemisphere at any times. These results indicate that following parasagittal fluid-percussion brain injury, the temporal expression of TNF-α mRNA is altered in specific brain regions, including those of the non-traumatzed hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) were prepared. Total RNA is isolated and Northern blot hybridization is performed and the quantity of brain tissue IL-1β mRNA is presented as percent relative radioactivity of IL-1β positive macrophage RNA which is loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic pathologic or regenerative sequelae of brain injury.

The above description fully discloses the invention including preferred embodiments thereof Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:
1. A method of treating a CSBP/RK/p38 kinase mediated disease in a mammal in need thereof, which comprises administering to said mammal an effective amount of a compound of Formula (III)

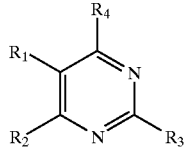

(III)

wherein:
- $R_1$ is 4-pyridyl, 4-pyrimidinyl, 4-quinazolinyl, 4-quinolyl, or 6-isoquinolinyl ring, which ring is optionally substituted with one or two substituents, each of which is independently selected from Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, amino, mono and di-$C_{1-6}$ alkyl substituted amino, or $N(R_{10})C(O)R_b$;
- Y is $X_1$—$R_a$;
- $X_1$ is oxygen or sulfur;
- $R_a$ is $C_{1-6}$alkyl, aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally substituted;
- $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl, wherein each of these moieties may be optionally substituted;
- $R_2$ is an optionally substituted aryl or optionally substituted heteroaryl group, provided that both $R_1$ and $R_2$ are not the same heteroaryl group; wherein when one $R_2$ is an optionally substituted aryl ring, the ring is substituted by one or two substituents, each of which is independently selected, and which, for a 4-phenyl, 4-naphth-1-yl or 5-naphth-2-yl substituent, is halo, cyano, $C(Z)NR_{13}R_{14}$, $C(Z)OR_{23}$, $(CR_{10}R_{20})_n$ $COR_{36}$, $SR_{15}$, $S(O)R_{15}$, $OR_{36}$, halo-substituted-$C_{1-4}$ alkyl, $C_{1-4}$ alkyl, $ZC(Z)R_{36}$, $NR_{10}C(Z)R_{23}$, or $(CR_{10}R_{20})_n$ $NR_{10}R_{20}$ and which, for other positions of substitution, is halo, cyano, $C(Z)NR_{16}R_{26}$, $C(Z)OR_8$, $(CR_{10}R_{20})_n$ $COR_8$, $S(O)_mR_8$, $OR_8$, halo-substituted-$C_{1-4}$ alkyl, $C_{1-4}$ alkyl, $(CR_{10}R_{20})_n NR_{10}C(Z)R_8$, $NHS(O)_mR_7$, $NHS(O)_m$ $NR_{13}R_{14}$, $NR_7S(O)_mR_7$, $NR_7S(O)_mNR_{13}R_{14}$, $ZC(Z)R_8$ or $(CR_{10}R_{20})_n$ $NR_{16}R_{26}$; and when $R_2$ is an optionally substituted heteroaryl group, the substituent groups include one or two substituents each of which is independently selected from $C_{1-4}$ alkyl, halo, $C_{1-4}$ alkoxy, $C_{1-4}$ alkylthio, $NR_{10}R_{20}$, or an N-heterocyclyl ring which ring has from 5 to 7 members and optionally contains an additional heteroatom selected from oxygen, sulfur or $NR_{12}$;
- m is 0 or an integer of 1 or 2;
- m' is an integer of 1 or 2;
- m" is an integer having a value of 1 to 10;
- n is 0 or an integer of 1 or 2;
- n' is 0 or an integer having a value of 1 to 10;
- n" is an integer having a value of 1 to 10
- $R_3$ is hydrogen, $C_{1-10}$ alkyl, halosubstituted $C_{1-10}$ alkyl, $(CR_{10}R_{20})_{n'}Q$-$(Y_1)_t$, $(CR_{10}R_{20})_{n'}(Y_2)_p$, $(CR_{10}R_{20})_{n''}(Y_3)_p$, or $(CR_{10}R_{20})_{m''}(Y_4)_p$;
- p is 0 or an integer of 1 or 2;
- t is an integer of 1, 2, or 3;
- Q is an aryl or heteroaryl group;
- $Y_1$ is independently selected from hydrogen, halogen, $C_{1-5}$ alkyl, halo-substituted $C_{1-5}$ alkyl, $(CR_{10}R_{20})_n(Y_2)_p$, $(CR_{10}R_{20})_{n''}(Y_3)_p$, or $(CR_{10}R_{20})_{m''}(Y_4)_p$;
- $Y_2$ is halogen, $OR_8$, $S(O)_mR_{18}$, $SR_8$, $S(O)_{m'}OR_8$, $S(O)_m NR_8R_9$, or $O(CR_{10}R_{20})_n NR_8R_9$, $ZC(O)R_8$, or $OC(Z)NR_8R_9$;
- $Y_3$ is $NR_8R_9$, $NR_{10}C(Z)R_8$, $NR_{10}C(Z)NR_8R_9$, $NR_{10}S(O)_m R_{18}$, $N(OR_{21})C(Z)NR_8R_9$, $N(OR_{21})C(Z)R_8$, $NR_{10}C(=NR_{11})SR_{18}$, $NR_{10}C(=NR_{11})NR_8R_9$, $NR_{10}C(=CR_{14}R_{24})SR_{18}$, $NR_{10}C(=C(R_{24})_2)NR_8R_9$, $NR_{10}C(O)C(O)NR_8R_9$, $NR_{10}C(O)C(O)OR_{10}$, $NR_{10}S(O)_m CF_3$, or $NR_{10}C(Z)OR_{10}O$;
- $Y_4$ is $C(O)R_8$, $CO_2R_8$, $CO_2(CR_{10}R_{20})_{m''}CONR_8R_9$, CN, $C(Z)NR_8R_9$, $C(Z)NR_8OR_9$, $C(=NOR_{21})R_8$, $C(=NR_{19})NR_8R_9$, $C(=NOR_{19})NR_8R_9$, $C(=NR_{19})ZR_{18}$, $NR_{10}S(O)_m CF_3$, or $NR_{10}OC(Z)OR_{10}O$;
- $R_4$ is hydrogen, $NR_5R_6$, $NHS(O)_2R_7$, $NR_{10}C(Z)R_8$, $NR_{10}C(Z)NR_5R_6$, $NR_{10}C(=NR_{11})NR_5R_6$, or $NR_{10}C(Z)OR_{10}$; wherein the aryl, arylalkyl, heteroaryl, heteroaryl alkyl, heterocyclic and heterocyclic alkyl moieties of $R_7$, and $R_8$ may be optionally substituted;
- $R_5$ and $R_6$ are each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{17}$;
- Z is oxygen or sulfur;
- $R_7$ is $C_{1-10}$ alkyl, $C_{3-7}$ cycloalkyl, aryl, arylalkyl, heterocyclyl, heterocyclyl-$C_{1-10}$alkyl, heteroaryl or heteroarylalkyl;
- $R_8$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;
- $R_9$ is hydrogen, $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl or $R_8$ and $R_9$ may together with the nitrogen to which they are attached form a heterocyclic ring of 5 to 7 members which ring optionally contains an additional heteroatom selected from oxygen, sulfur or $NR_{17}$;
- $R_{10}$ and $R_{20}$ is each independently selected from hydrogen or $C_{1-4}$ alkyl;
- $R_{11}$ is hydrogen, cyano, $C_{1-4}$ alkyl, $C_{3-7}$ cycloalkyl or aryl;
- $R_{12}$ is $R_{10}$ or C(Z)—$C_{1-4}$ alkyl;
- $R_{13}$ and $R_{14}$ is each independently selected from hydrogen or $C_{1-4}$ alkyl or $R_{13}$ and $R_{14}$ together with the nitrogen to which they are attached form a heterocyclic ring of 5 to 7 members which ring optionally contains an additional heteroatom selected from oxygen, sulfur or $NR_{22}$;
- $R_{15}$ is hydrogen, $C_{1-4}$ aikyl, $C_{2-4}$ alkenyl, $C_{2-4}$ alkynyl or $NR_{13}R_{14}$, provided that the moiety $SR_{15}$ is not $SNR_{13}R_{14}$ and the moiety $S(O)R_{15}$ is not —SOH;
- $R_{16}$ and $R_{26}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_{17}$;
- $R_{17}$ is hydrogen, $C(Z)R_8$ or optionally substituted $C_{1-10}$ alkyl, $S(O)_2R_7$, optionally substituted aryl or optionally substituted aryl-$C_{1-4}$ alkyl;
- $R_{18}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl;

$R_{19}$ is hydrogen, $C_{1-10}$ alkyl, cycloalkyl, heterocyclyl, aryl, arylalkyl, heteroaryl or heteroarylalkyl;

$R_{21}$ is hydrogen, a pharmaceutically acceptable cation, $C_{1-10}$ alkyl, $C_{3-7}$ cycloalkyl, aryl, aryl $C_{1-4}$alkyl, heteroaryl, heteroarylalkyl, heterocyclyl, aroyl, or $C_{1-10}$ alkanoyl;

$R_{22}$ is $R_{10}$ or $C(Z)$—$C_{1-4}$ alkyl;

$R_{23}$ is $C_{1-4}$ alkyl, halo-substituted-$C_{1-4}$ alkyl, or $C_{3-5}$ cycloalkyl;

$R_{24}$ is independently selected from hydrogen, alkyl, nitro or cyano;

$R_{36}$ is hydrogen or $R_{23}$; provided that $R_3$ and $R_4$ are not both hydrogen;

or a pharmaceutically acceptable salt thereof.

2. The method according to claim 1 wherein $R_1$ is an optionally substituted 4-pyridyl or 4-pyrimidinyl.

3. The method according to claim 1 wherein $R_2$ is an optionally substituted phenyl.

4. The method according to claim 3 wherein the one or more optional substituents are independently selected from halogen or methoxy.

5. The method according to claim 1 wherein $R_4$ is $NR_5R_6$, $NHS(O)_2R_7$, $NR_{10}C(Z)R_8$, or $NR_{10}C(Z)NR_5R_6$.

6. The method according to claim 5 wherein $R_5$ and $R_6$ are hydrogen or optionally substituted $C_{1-4}$ alkyl.

7. The method according to claim 1 wherein $R_3$ is hydrogen, $(CR_{10}R_{20})_{n'}Q(Y_1)_t$, $(CR_{10}R_{20})_{n'}(Y_2)_p$, $(CR_{10}R_{20})_{n''}(Y_3)_p$, or $(CR_{10}R_{20})_{m''}(Y_4)_p$; Q is an aryl; and t is 1.

8. The method according to claim 1 wherein the CSBP/RK/p38 kinase mediated disease is psoriatic arthritis, Reiter's syndrome, rheumatoid arthritis, traumatic arthritis, rubella arthritis and acute synovitis, rheumatoid spondylitis, osteoarthritis, gouty arthritis, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption disease, osteoporosis, restenosis, cardiac and renal reperfusion injury, thrombosis, glomerularnephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis.

9. The method according to claim 1 wherein the CSBP/RK/p38 kinase mediated disease is sepsis, septic shock, endotoxic shock, gram negative sepsis, or toxic shock syndrome.

10. The method according to claim 1 wherein the CSBP/RK/p38 kinase mediated disease is Alzheimer's disease, or cerebral malaria.

11. The method according to claim 1 wherein the CSBP/RK/p38 kinase mediated disease is asthma, adult respiratory distress syndrome, cerebral malaria, chronic pulmonary inflammatory disease, silicosis, or pulmonary sarcososis.

12. The method according to claim 1 wherein the CSBP/RK/p38 kinase mediated disease is inflammatory bowel disease, Crohn's disease, or ulcerative colitis.

13. The method according to claim 1 wherein the CSBP/RK/p38 kinase mediated disease is eczema, contact dermatitis, psoriasis, sunburn, or conjunctivitis.

14. The method according to claim 1 wherein the CSBP/RK/p38 kinase mediated disease is bone resorption disease, or osteoporosis.

15. The method according to claim 1 wherein the CSBP/RK/p38 kinase mediated disease is restenosis, cardiac and renal reperfusion injury, thrombosis, glomerularnephritis, or diabetes.

16. The method according to claim 1 wherein the CSBP/RK/p38 kinase mediated disease is graft vs. host reaction, allograft rejection, multiple sclerosis, or muscle degeneration.

* * * * *